United States Patent [19]
Dannoux et al.

[11] Patent Number: 6,030,829
[45] Date of Patent: Feb. 29, 2000

[54] HIGH DENSITY TEST PLATE AND PROCESS OF MAKING

[75] Inventors: Thierry Luc Alain Dannoux, Avon; Gilbert Dominique Pujol, Dammarie les Lys, both of France; David Martin Root, Lexington, Mass.

[73] Assignee: Corning Incorporated, Corning, N.Y.

[21] Appl. No.: 08/747,425

[22] Filed: Nov. 20, 1996

[30] Foreign Application Priority Data

Nov. 22, 1995 [FR] France .................................. 95 13878

[51] Int. Cl.⁷ ...................................................... C12M 1/34
[52] U.S. Cl. ......................... 435/288.3; 65/106; 65/255; 220/501; 428/152; 428/34.4; 435/288.5; 435/288.7
[58] Field of Search .................................. 65/93, 94, 106, 65/255, 273, 24; 428/152, 34.4; 215/6; 220/507; 435/288.3, 288.5, 288.7; 425/338

[56] References Cited

U.S. PATENT DOCUMENTS

| | | | |
|---|---|---|---|
| 1,528,194 | 3/1925 | Burgess | 65/255 |
| 1,653,524 | 12/1927 | Webb | 264/297.4 X |
| 3,238,031 | 3/1966 | Nikoll | 65/255 X |
| 3,847,582 | 11/1974 | Kozmin | 65/33 |
| 3,852,133 | 12/1974 | Houston | 156/3 |
| 3,961,929 | 6/1976 | Stockdale | 65/35 |
| 4,146,600 | 3/1979 | Elly et al. | 264/39 |
| 4,599,315 | 7/1986 | Terasaki et al. | 435/301 |
| 4,800,164 | 1/1989 | Bisconte | 435/300 |
| 5,049,177 | 9/1991 | Nakata | 65/93 |
| 5,090,982 | 2/1992 | Bradshaw et al. | 65/24 |

FOREIGN PATENT DOCUMENTS

| | | |
|---|---|---|
| 206597 | 12/1959 | Austria . |
| 0 493 202 A1 | 12/1991 | European Pat. Off. . |
| 0 580 112 A1 | 7/1993 | European Pat. Off. . |
| 72 34480 | 9/1972 | France . |
| 91 09152 | 7/1991 | France . |
| 48-20602 | 2/1973 | Japan . |
| 2179343 | 3/1987 | United Kingdom . |
| WO 89/05507 | 3/1988 | WIPO . |

*Primary Examiner*—Stanley S. Silverman
*Assistant Examiner*—Sean Vincent
*Attorney, Agent, or Firm*—Thomas R. Beall

[57] ABSTRACT

A support plate and method of making a support plate for biological or chemical testing or cell culture. The plate has a high density network of microwells formed therein. The wells are formed by a contact pressing technique whereby a network of protuberances are pressed into the surface of a thermoformable material.

23 Claims, 2 Drawing Sheets

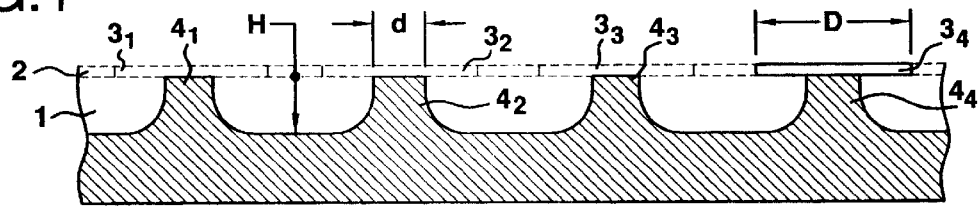
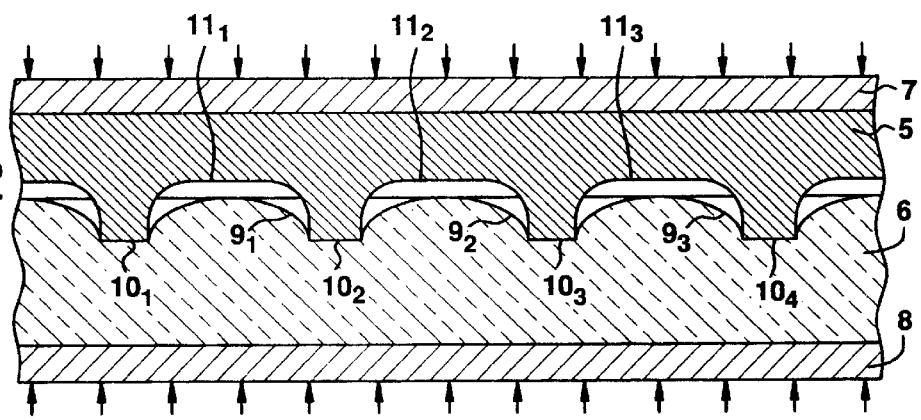
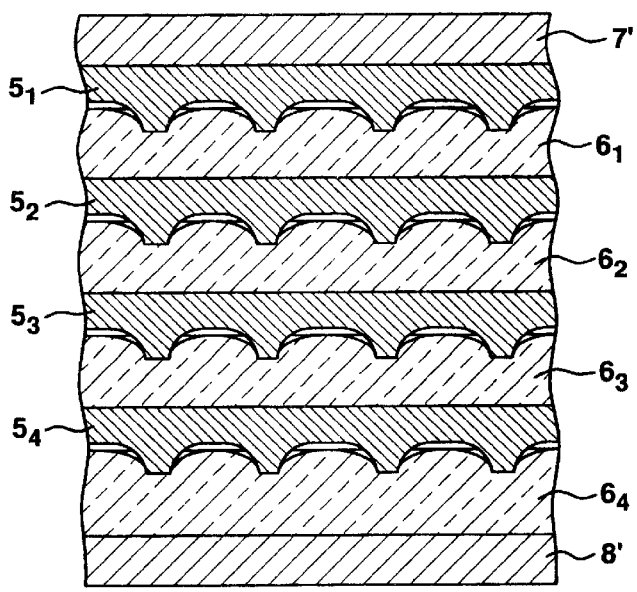
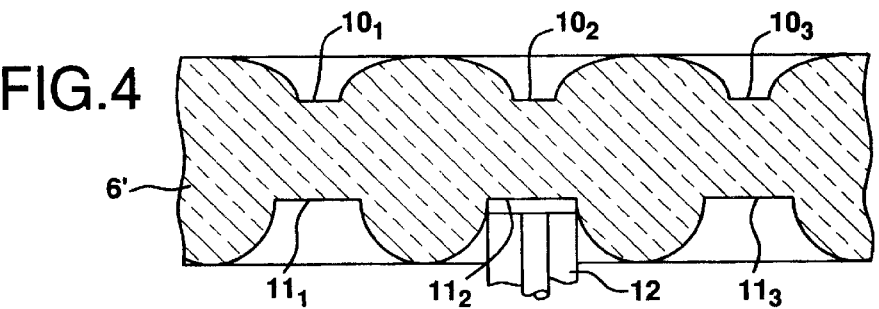

HIGH DENSITY TEST PLATE AND PROCESS OF MAKING

The present invention relates to process for manufacturing of a support plate for a two dimensional network of microwells, more particularly intended for the execution of biological tests or cultures. The present invention also relates to the microwell plate obtained by implementation of this process.

In order to execute biological tests of cultures, one currently uses plates molded out of thermoplastic materials such as a polycarbonate or polystyrene, these plates having 96 cavities or wells suitable for receiving, for example, cells to be grown and their nutritive medium. Typically, the plate is rectangular, with an approximately 80×125 mm format, and the wells have a diameter of approximately 8 mm. These dimensions provide about 8 mm on average. These dimensions are standardized so as to allow for automatic handling of the plates in apparatuses such as a liquid handling robot, a spectrophotometer, or a microscope for observation.

When such plates are used to perform genetic operations such as grafting of a "probe" on a segment of a DNA molecule, for example, the large volume of the well in comparison with the dimensions of a cell containing such a molecule, because of the relative concentration, lowers the probability of interaction of the probe and the molecule. Furthermore, the small number (96) of wells limits the number of tests or cultures which can be executed on the same plate.

The filling of the wells is currently done using pipette assemblies with a high cost of production and requiring specialized personnel for their handling. Each well receives a large number of cells. The grafting of a probe on a DNA molecule of one of them is then randomly carried out, whereas it would be preferable for this grafting to be carried out between a probe and a single cell, which are arranged near one another in a small well in order to increase the probability of execution of the grafting.

Observation of cultures is done through the bottom of the wells, which consists of a transparent membrane or textured or porous wall such as a screen or a fabric. Such means of forming the bottoms of the wells can hinder observation in polarized light, which is often desired, particularly in the case of membranes made of plastic material, which are capable of disturbing the polarization of the observation beam.

The plates mentioned above are currently produced by injection molding of a plastic material. It is known that molding of this type often involves the use of additives, such as lubricants (paraffin, for example) in order to improve the flow properties of the plastic material. Such an additive can later exude into the wells, disturbing the cultures. Other additives, such as products for stabilization of the plastic material with regard to ultraviolet radiation, can also exude and poison the cell cultures. On the other hand, numerous plastic materials exhibit fluorescence, which interferes with the observation of the tests.

There is also known a process for production of a plate made of silicon which, by a conventional process of etching used in the manufacturing of integrated circuits, is hollowed with a two-dimensional network of wells of very small diameter or "microwells," the density of these microwells per unit of surface area being much greater than that of the wells of the 80×125 mm plates described above. The microwells can be filled by wetting of an extended surface of the plate and then removal of the moisture from this plate with retreat of the liquid deposited at the bottom of the microwells. The microwells are delimited by sharp edges which work against the removal of moisture from the surface of the plate by blocking the drops of liquid which flow on the surface of the plate during this moisture removal.

Such silicon plates are fragile, and their manufacturing is delicate, long and costly. Furthermore, since silicon is a particularly opaque material, it is not possible to perform optical observations or measurements through the bottom of the microwells.

Other techniques can be envisaged for producing plates hollowed with a dense network of microwells, for example, the injection molding of the thermoplastic material such as a polycarbonate. The fluorescence of this material and the incorporation, conventional in itself, of lubricants and ultraviolet radiation stabilizers makes it unsuitable for the application in consideration here. It is also possible to think of proceeding by laser machining in order to produce microboring of a substrate. But then one observes burrs and roughness on the substrate, such that the surface condition of the plate obtained is favorable for the trapping of bubbles and does not offer the quality required to allow moisture to be removed from it.

The present invention therefore aims to provide a process for manufacturing of a plate supporting a very dense two-dimensional network of microwells of very small dimensions, on the order of the dimensions of the living cells which they are supposed to receive, which ensures easy filling of at least certain ones of the microwells with a small number of cells per microwell, with it possible for the number of wells formed on the plate to be very large so as to allow the execution of a large number of microbiological cultures on the same plate.

The present invention also aims to provide such a process allowing one to produce plates of microwells made of a material with a high degree of chemical neutrality on the surface, not containing or exuding any product capable of disturbing the cultures or hindering their observation These aims of the invention, as well as others which will appear upon reading of the following description, are reached with a process for manufacturing of a support plate for a two-dimensional network or microwells for microbiological cultures, which is remarkable in that a) a pressing matrix is formed, made of a nondeformable material with a surface from which projects a two-dimensional network of protuberances isolated from one another and having ends corresponding to the bottoms of the microwells to be formed, these protuberances having a height greater than the depth of said microwells, b) a plate made of a thermoformable material, heated above its softening temperature, is pressed against said matrix surface in such a way that only the protuberances come in contact with said plate and are then sunk into it to a depth equal to that of the microwells to be formed in this plate, and less than the height of these protuberances, and c) said plate is cooled in order to obtain a stable network of microwells on it.

As will subsequently be seen, this process allows one to produce, in a not very expensive manner, in an inert and transparent material such as glass, a network of microwells suitable for receiving cells to be grown in close proximity to probes, according to one of the essential aims of the invention. The network can be very dense and, for example, have $10^4$ times more wells as the 80×125 mm plate mentioned above over the same surface area, which allows one to multiply the number of cultures. As an illustrative and nonlimiting example, it is thus possible to manufacture a network of microwells approximately 100 $\mu$m apart from one another, these wells having a depth of 20 $\mu$m and a diameter at the bottom of 40 μm, making it possible to receive a 10 μm cell to be grown, for example. As will also subsequently be seen, the filling of the microwells occurs by a wetting-moisture removal operation which is particularly convenient and effective.

According to another characteristic of the process according to the invention, the pressing matrix is formed by chemical etching of a metallic plate through a mask consisting of a grid of areas centered on the axes of the protuberances to be obtained.

According to an advantageous variant of the process according to the invention, a number of matrixes are formed, they are stacked with insertion of a plate made of thermoformable material between two adjacent matrixes, and the whole stack thus formed is hot pressed in order to obtain a number of plates, each hollowed with a network of microwells.

The process according to the invention allows one to obtain a plate which bears, on at least one of its surfaces, a network of microwells with an axial section in the form of a funnel which is flared starting from the bottom of the microwell, these bottoms being separated by surfaces which are convex at any point and free of any discontinuity of curvature, these surfaces moreover having a finish of optical quality. This geometry and this finish contribute towards concentrating the liquid products or other products deposited on the plate at the bottom.

Other characteristics and advantages of the process and of the plate according to the invention will appear upon reading of the following description and upon examination of the appended drawing in which:

BRIEF DESCRIPTION OF THE DRAWINGS

FIG. 1 is a diagrammatic and enlarged cross section of a part of a pressing matrix used in the process according to the invention, this view also illustrating its process of manufacturing, FIG. 2 diagrammatically illustrates the process for manufacturing of the network of microwells according to the invention, FIG. 3 diagrammatically illustrates an advantageous variant of the process of manufacturing represented in FIG. 2, allowing one to produce several networks simultaneously, FIG. 4 is an enlarged view in cross section of a part of a plate according to the invention, which has two networks of microwells, each formed on one of its two opposite surfaces.

Thus, as indicated above, the process for manufacturing of a support plate for a network of microwells according to the invention calls for a matrix which allows one to form these microwells by pressing of a plate made of thermoformable material heated to above its softening temperature. This material can be a glassy material such as glass, or a transparent plastic material.

In order to produce this matrix, according to a preferred mode of implementation of the invention, one starts with plate 1 made of a stable metallic alloy such as Nicrimphy of IMPHY SA.

A surface of metallic plate 1 is covered with a photosensitive resin which is exposed and strips off, by a conventional technique of photolithography, in such a way as to leave remaining on the surface of the plate a mask with the form of a regular grid of areas such as those referenced $3_1$, $3_2$, $3_3$, . . . in FIG. 1, with a roughly circular shape, for example.

Plate 1 is then chemically etched through this mask, using an etching solution which does not attack the resin of areas $3_i$*. In order to etch the Nicrimphy, it is possible to use a solution of iron perchloride with addition of 20 to 30% nitric acid. It is known that the isotropic attack of the metal of plate 1 by the etching solution dissolves the metal under area $3_i$ over a distance H equal to the desired etching depth. If one then wishes a network of protuberances $4_i$ with an end diameter d to appear on the surface of plate 1, it is then necessary to expose the photosensitive resin in such a way as to cause the appearance, after stripping, of areas $3_i$ of resin with diameter D such that:

$$D \cong d + 2H$$

* Editor's note: With the exceptions of $4_i$, and $10_i$ in FIGS. 5 and 6 respectively, no subscript "i" occurs in any of the figures. Therefore, subscript i should in many cases probably be read as subscript 1.

Figure 5:
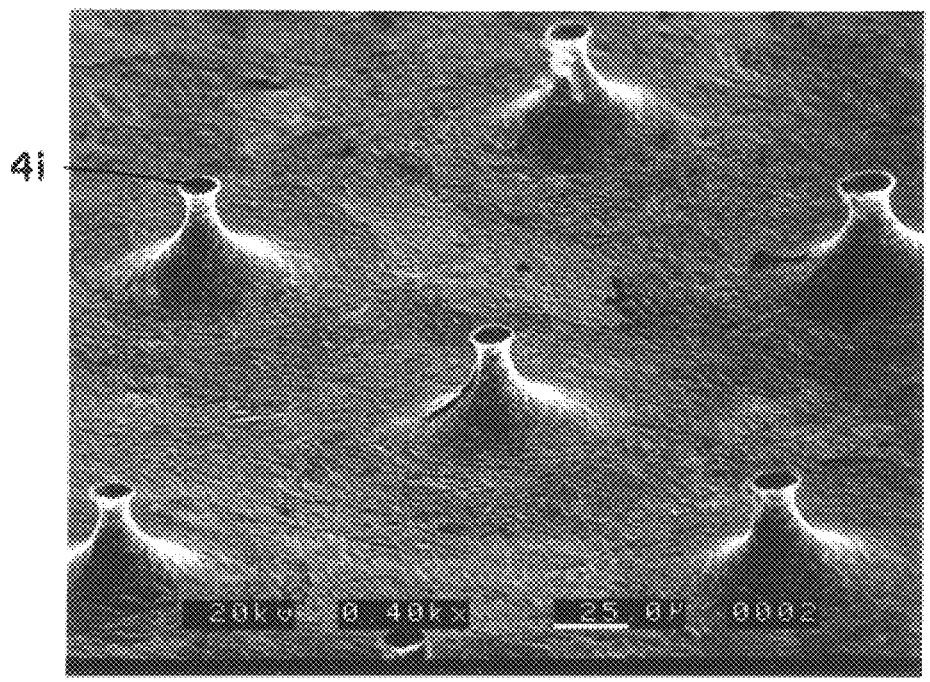
FIG. 5 is a picture taken with the scanning electron microscope of a part of the surface of the matrix used in the process according to the invention.

With the etching of the metal finished, areas $3_i$ of resin are removed with a suitable solvent, and the etched surface of plate 1 then has the appearance illustrated by the view of FIG. 5, taken with the scanning electron microscope. In this view appears a regular network of protuberances $4_i$ flared starting from their end and rejoining a bottom whose roughness is apparent in the view presented.

Plate 1 thus etched constitutes pressing matrix 5 which can be used in the process for manufacturing of plates of microwells according to the invention, illustrated in FIG. 2. Typically, the protuberances are approximately 100 to 200 μm apart, are 20 to 50 μm high, and have an end diameter between 20 and 50 μm.

For this purpose, as represented diagrammatically in this figure, one applies the etched surface of matrix 5 against plate 6 made of a thermoformable material heated to a sufficient temperature for it to have suitable plasticity or viscosity to be pressed. This material can be a plastic material, or more preferably, glass such as that referenced 7059 in the catalogues of the company Corning Incorporated. In the latter case, matrix 5 and glass plate 6 are placed in a furnace and gradually brought to a temperature of 740° C., so that the glass has a viscosity of approximately $10^{10}$ P. At this viscosity, suitable pressing of the matrix 5-plate 6 assembly using pressure plates 7,8 for approximately 1 min, causes protuberances $4_1$ of the matrix to penetrate into glass plate 6 to a depth which can be controlled so that glass surface elements $9_1$, $9_2$, $9_3$, . . . separating the wells $10_1$, $10_2$, $10_3$, . . . hollowed by protuberances $4_1$ in plate 6 in the plastic state, keep an "optical" finish because of the absence of any contact with surface elements $11_1$, $11_2$, . . . of the relatively rough bottom of the matrix.

Figure 6:
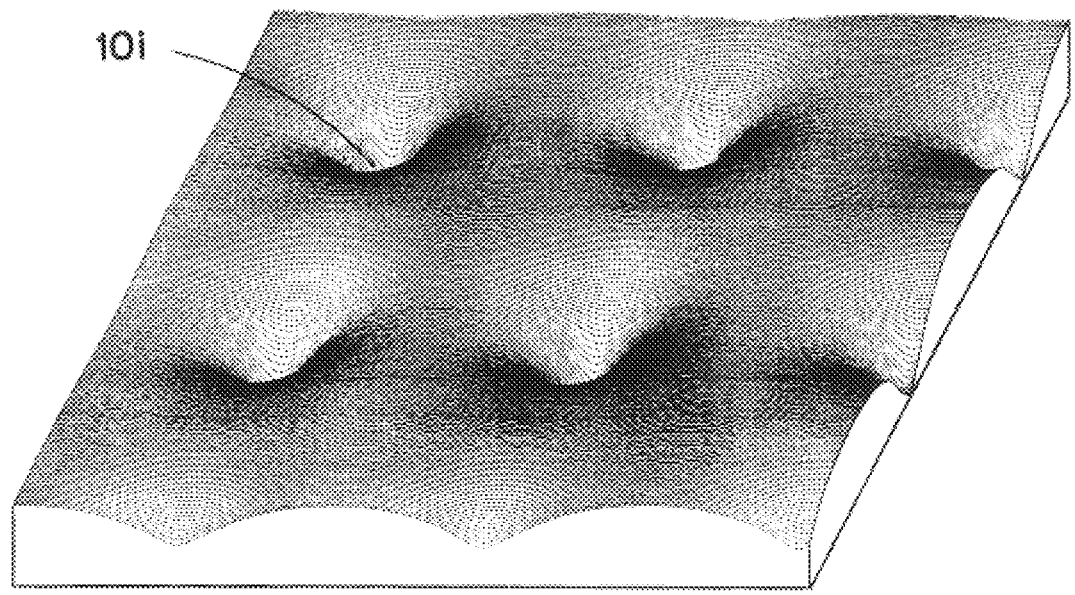
FIG. 6 is a view taken with the scanning mechanical microscope of a part of a plate obtained by implementation of the process according to the invention.

After cooling of plate 6 to room temperature, this plate bears a regular two-dimensional network of microwells $10_i$ such as those which appear in FIG. 6, which is a view of the surface of the plate taken with the scanning mechanical microscope.

In this view, it appears that the wells have a funnel shape, regularly flared from the bottom of the wells towards their openings on the surface of the plate, the bottoms being separated by surfaces which are convex at any point, which are free of any discontinuity of curvature, and have a finish of optical quality. It should be observed that these surfaces converge regularly towards the bottoms of the adjacent microwells.

Thanks to these shape and surface properties, it is easy to fill the microwells with cells to be grown, carried, for example, in a nutritive medium. A drop of a medium thus loaded with cells deposited on the surface of the plate in such a way as to "wet" the plate, the medium and the cells are "sucked" towards the bottoms of the wells by a process of "moisture removal" of the curved and smooth surfaces bordering the wells. The excess can be evacuated by controlled evaporation. The plate is then protected by a thin sheet of glass.

The process according to the invention allows one to produce plates with a very high density of microwells, for example $10^4$ wells per $cm^2$. It is possible then, by the process of wetting-moisture removal described above, to provide a very large number of microwells with cells to be grown and their nutritive medium, the "probes" having been previously deposited according to a predetermined cartography in the wells. Typically, as an example, the microwells can have a depth of 15 to 30 $\mu$m, the diameter of the bottom of the wells being in the range of 20–50 $\mu$m, and the distance between the wells being approximately 100 to 200 $\mu$m. It is understood that a cell, typically approximately 10 $\mu$m, is then found at the bottom of a well very close to the probes introduced beforehand into this well, which very advantageously increases the probability of the desired grafting.

Texturing of the bottom of the microwells facilitates suction and retaining of the cells and drops of liquid deposited on the surface of the plate of microwells. This texturing can be obtained, according to the invention, by rolling, brushing, polishing, glazing, shot-peening, ion bombardment, for examples of the surface of the metal plate used to produce the pressing matrix, before deposition of the photosensitive resin intended for the formation of the etching mask. Thus, the end surfaces of protuberances $4_i$ formed later by chemical etching, have a texture, the copy of which is printed on the bottom of the microwells during pressing of plate 6 according to the invention.

The end surfaces of the protuberances could also be hollowed, by "Eximer" laser etching, for example, with identification marks such as numbers or bar codes, for example, marks whose copy is transferred to the bottoms of the microwells at the time of pressing of the plate, as described above. The marking of the various cultures carried by the plate is facilitated by these means.

The plate of microwells according to the invention can carry other marks allowing for automatic identification of the plate in apparatuses for manipulation or treatment. These marks can also be formed during pressing by copying corresponding marks formed on the matrix.

It should be observed that the present invention allows one to make it so that the bottoms of the wells of the same plate are all coplanar, which facilitates focusing of a microscope for observation of these cultures.

In this regard, the network of microwells can have lines or columns of microwells with bottoms whose shape, for example, oval, differs from that of the others (for example, circular). These lines and columns, regularly distributed, provides a meshwork for the network which can be observed with the microscope, which facilitates exploration of the network and identification of the cultures made in the microwells.

Techniques of pressing other than the static pressing illustrated in FIG. 2 could be used to manufacture the plate of microwells according to the invention, for example, rolling, blowing, or suction of a material in the plastic state, against a matrix according to the invention.

A variant of the process according to the invention is illustrated in FIG. 3. According to this variant, several matrixes $5_1$, $5_2$, $5_3$, . . . which are stacked with insertion of plate $6_1$, $6_2$, $6_3$, . . . made of thermoplastic material between two adjacent matrixes. The whole is heated and then pressed as described above in connection with FIG. 2. This variant has two advantages: on one hand, it increases the productivity of the process, and, on the other hand, it improves the regularity of the pressing operations done on the various plates $6_i$ by the "mattress" effect resulting from the stacking of the plates, an effect which is favorable for making the pressure applied on the plates uniform.

A variant of the plate of microwells according to the invention is represented in FIG. 4, by a cross section of this plate according to a plane perpendicular to its surface. The section represented shows that each of the two surfaces of plate 6' has a network of microwells $10_1$, $10_2$, . . . and $11_1$, $11_2$, . . . respectively. The network of microwells $10^i$ roughly corresponds to that of the plate of FIG. 2. Microwells $11^i$, . . . formed on the other surface of the plate are each centered on the axis of a microwell $10_i$. Their size is determined so as to receive a means of treatment (by heating, for example) or of observation of the culture performed in the corresponding microwell $10_i$. This means can take the form of one or more optical fibers 12, for example, in the case of automatic analyses by fluorescence or colorimetry.

The two networks of microwells can be used to execute cultures. Flat glass plates applied against the networks of microwells can protect the cultures which are developed in them.

It now appears that the present invention indeed allows one to reach the aims and to obtain the advantages which were chosen. Thus, thanks to the great density of microwells formed in a plate and thanks to the geometry of these microwells, bordered by convex surfaces converging towards the bottoms of the adjacent wells, it is possible to easily fill a large number of wells with liquid media and cells necessary for a microbiological culture of these cells, for purposes of genetic engineering, for example.

The material preferably used for forming the plate, namely glass, contrary to the majority of the plastic materials, allows for observations of cultures in polarized light as well as in natural light, undisturbed by interfering fluorescence.

The high degree of chemical inertness of glass allows for the use of acetone, which is necessary for fixing the cells, or for the use of stains such as, for example, hematoxylin, which is necessary for observation of the contents of the nuclei, and at the same time, it prevents contamination by products coming from the material of the plate.

The excellent dimensional stability of glass contributes several other advantages: great precision (on the order of a micrometer) of identification of the wells on the plates, as well as of positioning of the plates in machines for the operation of treatments, easy focusing of an observation microscope on the flat and coplanar bottoms of the wells.

Using a velvet pad, it is possible to transfer simultaneously a part of the contents of each well in order to transfer them to another plate, which allows one to copy these cultures.

The flared shape of the microwells allows possible microbubbles of air to escape from the wells rather than to remain caught there, disturbing the cultures and the observations of which they are the object.

The very small size of the microwells allows one to execute, in each of them, monocellular cultures or cultures of a very small number of cells, allowing one to obtain clones whose paternity is certain. This small size of the wells increases the relative concentrations and promotes the probability of interaction of the probes (DNA fragments) with the molecules of DNA on which grafting is supposed to be done.

Polymerase chain amplification, commonly called PCR, which requires thermal cycling, would not be possible "in situ" with the plates made of thermoplastic material (for example, polystyrene) currently used for cell cultures, but it becomes possible with a glass plate because of the very good resistance of this material to such cyclings.

Finally, particularly advantageously, the invention allows one to manufacture support plates for very dense networks of microwells by a pressing process, allowing for manufacturing of said plates at industrial speeds and at particularly low actual manufacturing costs.

Of course, the invention is not limited to the embodiment described or represented, which was only given as an example. Thus, the plate according to the invention could also be produced with various plastic materials, insofar as the problems of contamination or difficulties of observation of the cultures mentioned above do not arise under the conditions of use of such a plate. A ductile metal capable of plastic deformation could also be used, if observations made through the bottoms of the microwells are not foreseen. Furthermore, the invention applies not only to the execution of biological cultures but also to the execution of any test or treatment of microsamples of any materials.

We claim:

1. A process for forming a plate having a plurality of seperate and distant wells imprinted therein for use in biological or chemical assays or cultures comprising the steps of
   a) providing a pressing matrix comprising a network of protuberances extending from a surface;
   b) pressing said network into a substantially flat plate of a glass material, said glass material having been heated above its softening temperature;
   c) removing said network; and
   d) cooling said flat plate.

2. The process of claim 1 wherein said pressing matrix is formed by chemical etching of a metallic plate, through a mask consisting of a grid of areas conforming to said network.

3. The process of claim 1 wherein said protuberances have a length of approximately 20–50 μm, have an end diameter of approximately 20–50 μm, and are located approximately 100–200 μm apart.

4. The process of claim 1 wherein said substantially flat plate is pressed against said network.

5. The process of claim 1 wherein said protuberances have raised identification marks formed on an end that engages said flat plate during said pressing step.

6. The process of claim 1 wherein said protuberances have a textured end surface that engages said flat plate during said pressing step.

7. The process of claim 1 wherein said pressing step is accomplished by means of static pressing.

8. The process of claim 1 wherein said pressing step is accomplished by means of rolling.

9. The process of claim 1 wherein said pressing step is accomplished by means of blowing.

10. The process of claim 1 wherein said pressing step is accomplished by means of suction.

11. A process for forming a plurality of plates having a plurality of seperate and distinct wells imprinted therein for use in biological or chemical assays or cultures comprising the steps of:
    a) providing a plurality of stacked pressing matrixes, each comprising a network of protuberances extending from a surface, each matrix separated by a space;
    b) inserting a plurality of plates of a glass material, each into one said space between said matrixes, said glass material having been heated above its softening temperature;
    c) pressing said pressing matrixes together such that said network from each matrix is pressed into the immediately adjacent plate;
    d) removing said plurality of networks from said plurality of plates; and,
    e) cooling said plurality of plates.

12. A plate for use in biological or chemical assays or cultures comprising:
    a glass plate having a surface having a network of seperate and distinct microwells formed therein,
    said microwells each having a bottom surface and an axial section in the form of a flared funnel starting from said bottom surface,
    whereby any portion of said surface separating two adjacent bottom surfaces is convex at any point and free of any discontinuity of curvature.

13. The plate of claim 12 wherein said surface and said bottom surfaces of said microwells have a finish of optical quality.

14. The plate of claim 12 wherein said bottom surfaces of said microwells are textured.

15. The plate of claim 12 wherein said bottom surfaces of said microwells have identifying impressions marked therein.

16. The plate of claim 12 wherein said bottom surfaces of said microwells are coplanar.

17. The plate of claim 12 wherein said network of microwells comprises a plurality of columns of microwells each column having microwells having bottoms surfaces whose shape differs from bottom surface shapes of microwells of other said columns.

18. The plate of claim 12 wherein the distance between bottom surfaces of adjacent well is approximately 100–200 μm apart.

19. The plate of claim 12 wherein said microwells have a depth of approximately 15–20 μm.

20. The plate of claim 12 wherein the diameter of the bottom surfaces is approximately 20–50 μm.

21. A plate for use in biological or chemical assays or cultures comprising:
    a glass plate having opposing surfaces, each surface having a network of seperate and distinct microwells formed therein,
    said microwells each having a bottom surface and an axial section in the form of a flared funnel starting from said bottom surface,
    whereby any portion of said surface separating two adjacent bottom surfaces is convex at any point and free of any discontinuity of curvature
    each microwell from one of said networks being coaxial with a corresponding microwell from the network formed in the opposing surface.

22. The plate of claim 21 wherein each microwell of one of said networks is configured so as to receive a means of observation.

23. The plate of claim 22 wherein said means of observation is an end of an optical fiber.

* * * * *